(12) United States Patent
Ono et al.

(10) Patent No.: US 8,142,821 B2
(45) Date of Patent: Mar. 27, 2012

(54) XANTHOHUMOL-ENRICHED HOP EXTRACT

(75) Inventors: Mitsunori Ono, Lexington, MA (US); Naoto Yamaguchi, Takayama (JP); Keiko Yamaguchi, Takayama (JP)

(73) Assignee: Flazan GmbH & Co. KG, Nurnberg (DE)

( * ) Notice: Subject to any disclaimer, the term of this patent is extended or adjusted under 35 U.S.C. 154(b) by 0 days.

(21) Appl. No.: 12/422,146

(22) Filed: Apr. 10, 2009

(65) Prior Publication Data

US 2009/0258094 A1 Oct. 15, 2009

Related U.S. Application Data

(63) Continuation-in-part of application No. 12/190,965, filed on Aug. 13, 2008, now Pat. No. 7,833,552.

(60) Provisional application No. 60/955,906, filed on Aug. 15, 2007.

(51) Int. Cl.
*A01N 65/00* (2009.01)
(52) U.S. Cl. .................................................. 424/725
(58) Field of Classification Search ................. None
See application file for complete search history.

(56) References Cited

U.S. PATENT DOCUMENTS

| | | |
|---|---|---|
| 3,892,808 A | 7/1975 | Mitchell |
| 6,867,332 B1 | 3/2005 | Biendl et al. |
| 2004/0121040 A1 | 6/2004 | Forster et al. |
| 2005/0019438 A1 | 1/2005 | Bourges-Sevenier et al. |
| 2005/0042318 A1 | 2/2005 | Erdelmeier et al. |
| 2007/0110835 A1* | 5/2007 | Maes et al. .................. 424/778 |

FOREIGN PATENT DOCUMENTS

EP   1543834   6/2005

OTHER PUBLICATIONS

International Search Report issued in International Application No. PCT/US2008/073013, Feb. 16, 2009.

* cited by examiner

*Primary Examiner* — Michael Meller
(74) *Attorney, Agent, or Firm* — Edwards Wildman Palmer LLP; Jeffrey D. Hsi; Melissa Hunter-Ensor, Esq.

(57) ABSTRACT

A method for preparing a xanthohumol-rich hop composition. The method includes providing a solution that contains xanthohumol-containing hop substances and effecting precipitation of non-xanthohumol hop substances by adjusting both the salt concentration and pH value of the solution. The xanthohumol-rich hop composition prepared by this method can be used for treating various diseases, e.g., skin disorders, and bacterial infection.

10 Claims, 2 Drawing Sheets

Fig. 1. Structures of hop components (1–7).

XANTHOHUMOL-ENRICHED HOP EXTRACT

CROSS-REFERENCE TO RELATED APPLICATION PARAGRAPH

This application is a continuation-in-part of U.S. Utility application Ser. No. 12/190,965, filed Aug. 13, 2008 now U.S. Pat. No. 7,833,552, which claims the benefit of U.S. Provisional Application No. 60/955,906 filed on Aug. 15, 2007. The contents of which, is hereby incorporated by reference in its entirety.

BACKGROUND

Xanthohumol exists in hops, which are primarily used in brewery. As a strong antioxidant, it exhibits benefits in treating diseases associated with oxidative stress, e.g., cancer and neurodegenerative disorder.

A number of methods have been developed to prepare xanthohumol-containing hop extracts for medical uses. These methods, however, have several disadvantages. For example, hop extracts prepared by hitherto known methods contain a substantial amount of iso-xanthohumol, which is undesirable for its estrogen activity, or chlorophyll, which is undesirable for its green color. As another example, when supercritical $CO_2$ extraction is used, expensive facilities are required so as to reduce the danger of explosion.

Given the above disadvantages, it is highly desirable to develop a safe and inexpensive method for preparing from hops xanthohumol-rich compositions that contain little iso-xanthohumol and chlorophyl.

SUMMARY

This invention is based on an unexpected discovery that adjustment to certain salt concentrations and pH values of xanthohumol-containing solutions prepared from hops substantially salts out non-xanthohumol substances and thus enriching xanthohumol.

Accordingly, in one aspect, the present invention features a method of preparing from hops a composition having a high xanthohumol content. This method includes at least five steps: (1) providing a first solution containing hop substances that include 0.4-90% (e.g., 0.4-20%) by weight xanthohumol and a solvent that includes up to 90% by volume water and at least 3% by volume a water miscible solvent; (2) adjusting the salt concentration of the first solution to 0.05-5.0 M (e.g., 0.5-2.5 M) and its pH value to 9.5-13 (e.g., 10.5-12.0) to effect formation of a first precipitate; (3) removing the first precipitate to obtain a second solution; (4) adjusting the pH of the second solution to 3-9 (e.g., 7-8) to effect formation of a second precipitate; and (5) collecting the second precipitate that contains 40-95% by weight xanthohumol.

In this method, the first solution can be prepared by extracting raw hops (i.e., hop cones or hop flowers) or spent hops with a polar organic solvent, removing (completely or partially) the polar organic solvent to obtain a residue or a concentrated hop extract, and then dissolving the residue or the extract in another solvent, which can be water, a water miscible solvent, or a mixture thereof.

The first solution thus prepared or prepared by other methods is then subjected to adjustment of its salt concentration and pH to salt out non-xanthohumol substances, i.e., step (2). Adjustment of the salt concentration can be achieved by mixing the first solution with an aqueous salt solution. The pH value can be adjusted by adding to it a basic solution, e.g., NaOH or KOH. Step (4) also requires pH adjustment, which can be achieved with an acidic solution.

In one implementation of this method, salting-out is performed twice instead of once. See steps (2) and (4) below. This implementation includes at least the following seven steps: (1) providing a first solution containing hop substances that include 0.4-90% (0.4-20%) by weight xanthohumol and a solvent that includes up to 90% by volume water and at least 3% by volume a water miscible solvent; (2) adjusting the salt concentration of the first solution to 0.05-0.3 M to effect formation of a first precipitate; (3) removing the first precipitate to obtain a second solution; (4) adjusting the salt concentration of the second solution to 0.3-5.0 M and its pH to 9.5-13 to effect formation of a second precipitate; (5) removing the second precipitate to obtain a third solution; (6) adjusting the pH value of the third solution to 3-9 to effect formation of a third precipitate; and (7) collecting the third precipitate that contains 40-95% by weight xanthohumol.

In another aspect, this invention provides a composition containing at least 30% (e.g., 50% or 75%) by weight xanthohumol and 0.4-4.5% (e.g., 0.4-3.5%, 0.4-3.0%, 0.4-2.5%, or 0.4-1.5%) by weight isoxanthohumol. In one example, this composition is prepared by any of the methods described above.

In another aspect, the invention generally provides a method of preparing from hops a composition having a high xanthohumol content, the method involving providing a first solution containing hop substances and a first solvent, where the hop substances include 0.4-90% by weight xanthohumol and the first solvent includes up to 90% by volume water and at least 3% by volume a water miscible solvent; adjusting the salt concentration of the first solution to 0.05 M to 5.0 M and the pH value of the first solution to 9.5-13 to effect formation of a first precipitate; removing the first precipitate to obtain a second solution; adjusting the pH of the second solution to 3-9 to effect formation of a second precipitate; and collecting the second precipitate, where the second precipitate contains 40-95% by weight xanthohumol.

In another aspect, the invention provides a method of preparing a high xanthohumol content composition from hops, the method involving providing a first solution containing hop substances and a first solvent, where the hop substances include 0.4-90% by weight xanthohumol and the first solvent includes up to 90% water by volume and at least 10% by volume a water miscible solvent; adjusting the salt concentration of the first solution to 0.05 M to 0.3 M to effect formation of a first precipitate; removing the first precipitate to obtain a second solution; adjusting the salt concentration of the second solution to greater than 0.3 M to 5.0 M and the pH value of the second solution to 9.5 to 13 to effect formation of a second precipitate; removing the second precipitate to obtain a third solution; adjusting the pH of the third solution to 3-9 to effect formation of a third precipitate; and collecting the third precipitate, where the third precipitate contains xanthohumol 40-95% by weight.

In yet another aspect, the invention provides a xanthohumol-containing composition prepared by the method of a previous aspect.

In yet another aspect, the invention provides a dry hop extract containing at least 30%, 50% or 75% by weight xanthohumol and 0.4-4.5% (e.g., 0.4, 2.5%, 3.5%, 4.5%) by weight isoxanthohumol.

In yet another aspect, the invention provides a method of treating a skin disorder, cancer, alleviating inflammation, treating a viral or bacterial infection, diabetes, obesity, or lowering cholesterol in a subject. In each of the aforementioned conditions or any other condition delineated herein, the method involves administering to a subject in need thereof an effective amount of a xanthohumol-containing composition prepared by a method delineated herein. Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In yet another aspect, the invention provides a pharmaceutical composition formulated for topical administration containing xanthohumol and a pharmaceutically acceptable excipient, where the composition contains an isoxanthohumol/xanthohumol ratio that is 0.01-0.5 (e.g., 0.3 or 0.4). In one embodiment, the composition is a topical formulation selected from the group consisting of a solution, liniment, lotion, cream, ointment, paste, gel, and emugel. In another embodiment, the composition further contains a vitamin selected from the group consisting of vitamin B, 1,25-dihydroxy vitamin D3, vitamin K, vitamin A, and vitamin C. In yet another embodiment, the composition further contains an anti-microbial agent selected from the group consisting of tolnaftate, ketoconazole, erythromycin, and tetracycline. In yet another embodiment, the composition further contains an insect-repellent selected from the group consisting of aliphatic, cyclic or aromatic amides, citronella oil, terpineol, cineole, neem oil, and ethyl butyacetylaminopropionate. In yet another embodiment, the composition further contains a self-tanning agent selected from the group consisting of dihydroacetone and lawsone. In yet another embodiment, the composition further contains an anti-inflammatory agent selected from the group consisting of hydrocortisone, prednisone, prednisolone, aspirin, aloe vera, and mixtures thereof. In yet another embodiment, the composition further contains a topical analgesic selected from the group consisting of lidocaine, benzocaine, butacaine, and clove oil. In yet another embodiment, the composition further contains a skin redness reducer selected from the group consisting of guanidine derivatives and L-arginine derivatives.

In another aspect, the invention provides a method of treating a skin disorder, the method involving administering to a subject in need thereof an effective amount of a xanthohumol-containing composition prepared by a method delineated herein, where the skin disorder is acne, rosacea, eczema, psoriasis, atopic dermatitis, contact dermatitis, seborrhea, sunburn, or skin aging.

In yet another aspect, the invention provides a method of treating a skin disorder, the method involving administering to a subject in need thereof an effective amount of a xanthohumol-containing composition delineated herein, where the skin disorder is selected from the group consisting of acne, rosacea, eczema, psoriasis, atopic dermatitis, contact dermatitis, seborrhea, sunburn, or skin aging.

In various embodiments of any of the above methods or any other aspect of the invention delineated herein, a xanthohumol composition contains hop substances ranges from 0.4-20% by weight. In one embodiment of any previous aspect, a first solution is prepared by extracting hops or spent hops with a second solvent, removing the second solvent to obtain a residue, and dissolving the residue in the first solvent; where the second solvent is a polar organic solvent. In another embodiment, the water miscible solvent is selected from the group consisting of methanol, ethanol, propanol, butanol, pentanol, acetone, tetrahydrofuran, dimethylformamide, dimethylamine, and dimethyl sulfoxide. In yet another embodiment, the water miscible solvent is ethanol. In still another embodiment, the salt concentrations of the first and second solutions are adjusted by mixing them with an aqueous solution containing an inorganic salt selected from the group consisting of KCl, NaCl, $CaSO_4$, or $MgSO_4$. In still another embodiment, the salt concentrations of the first and second solutions are adjusted by mixing them with an aqueous solution containing an organic salt selected from the group consisting of citric acid salt tartaric acid salt, and acetic acid salt. In another embodiment, the salt concentration of the second solution is adjusted to 0.5-2.5 M. In another embodiment the pH value of the second solution is adjusted to 10.5-12.0. In another embodiment, the pH value of the third solution is adjusted to 7-8. In various embodiments of the invention, compositions delinated herein are useful for the treatment of a skin disorder that is not related to sun damage or aging.

Any of the xanthohumol-enriched compositions described above can be used for treating disease/disorder such as skin disorder, inflammatory disease, cancer, viral or bacterial infection, diabetes, obesity, and high cholesterol levels. To achieve the intended therapeutic effects, an effective amount of the composition is administered to a subject in need thereof. The term "treating" as used herein refers to the application or administration of a composition including one or more active agents to a subject, who has one of the diseases/disorders mentioned above, a symptom of the disease/disorder, or a predisposition toward the disease/disorder, with the purpose to cure, heal, alleviate, relieve, alter, remedy, ameliorate, improve, or affect the disease/disorder, the symptoms of the disease/disorder, or the predisposition toward the disease/disorder, "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with another active agent.

Also within the scope of this invention is use of any of the xanthohumol-enriched compositions described herein for the manufacture of a medicament for the just-mentioned treatments.

The details of one or more embodiments of the invention are set forth in the description below. Other features, objects, and advantages of the invention will be apparent from the description and from the claims.

DETAILED DESCRIPTION

Figure 1:
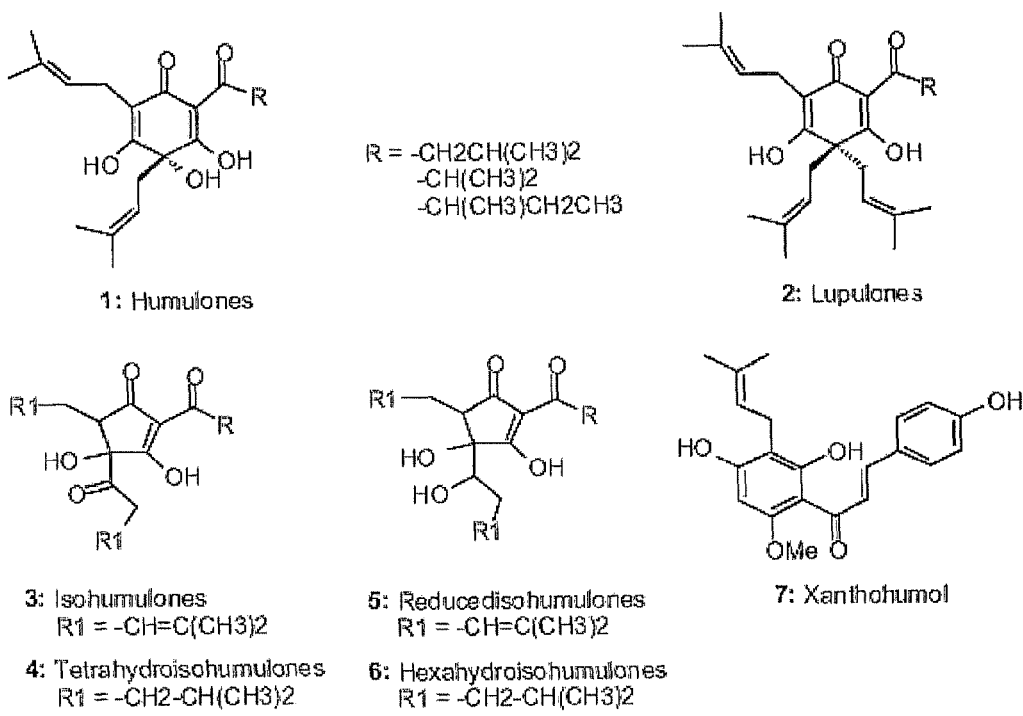
FIG. 1 shows structures of hop components (1-7).

The starting material for the method of this invention, i.e., a xanthohumol-containing solution (hereinafter "first solution"), can be prepared from xanthohumol-containing hop materials, e.g., hop cones, hop flowers, and spent hops. This solution contains a solvent such as water, a water miscible solvent, or a mixture thereof and hop substances including 0.5-90% by weight xanthohumol. The concentration of xanthohumol in the first solution can be 3% (w/v) or lower.

In one example, the first solution is prepared by extracting a xanthohumol-containing hop material with a water miscible solvent (e.g., ethanol or acetone). More specifically, the hop material is soaked in the water miscible solvent under a suitable temperature (e.g., 50° C.) for a sufficient period of time (e.g., 30 minutes) until xanthohumol is fully dissolved. The first solution is obtained by removing, e.g., via centrifugation or filtration, insoluble hop substances, and, optionally, removing part of the water miscible solvent such that the volume of the first solution is manageable.

In another example, the first solution is prepared as follows. A hop material, e.g., spent hops, is extracted with a polar organic solvent to produce a solution containing the organic solvent and hop substances dissolved therein. The polar organic solvent is an organic solvent having a polarity greater than that of ether. Exemplary polar organic solvents include, but are not limited to, ethanol, methanol, ethyl acetate, or acetone. Subsequently, the polar organic solvent is removed from the solution, e.g., by evaporation, to afford a dry or semi-dry hop extract, which can contain 0.4-20% by weight xanthohumol. If the polar organic solvent is a water miscible solvent, e.g., ethanol, the solvent can be only partially removed from the solution to afford a concentrated hop extract. The hop extract is then dissolved in water, a water miscible solvent, or a mixture thereof. The mixture can contain at least 3% (e.g., 10%, 50%, or 90%) by volume a water miscible solvent and up to 90% (e.g., 50%) by volume water. The ratio of water and the water miscible solvent in the mixture can be determined based on the amount of xanthohumol to be dissolved therein. Exemplary water miscible solvents include methanol, ethanol, propanol, butanol, pentanol, acetone, tetrahydrofuran, dimethylformamide, dimethylamine, and dimethyl sulfoxide.

The first solution can also be prepared by dissolving, in water a water miscible solvent, or a mixture thereof, a hop extract prepared by the method of the invention. In other words, a product prepared by this method can be subjected to the same method again to further enrich xanthohumol. Alternatively, the first solution can be prepared by dissolving, in water, a water miscible solvent, or a mixture thereof, a hop extract prepared by methods known in the art, e.g., supercritical $CO_2$ extraction (see US Patent Application 2004/0121040).

The first solution is then subjected to adjustment of its salt concentration and pH value to salt out non-xanthohumol substances. To adjust its salt concentration to 0.05 M to 5.0 M (e.g., 0.2-2.5 M or 0.5-1.0 M), the first solution can be mixed with an aqueous salt solution. The salt solution can contain either an inorganic salt (e.g., KCl, LiCl, NaCl, NaBr, KBr, LiBr, KI, LiI, $CaSO_4$, $MgSO_4$, and a quarterly ammonium salt), or an organic salt (e.g., citric acid salt, tartaric acid salt, and acetic acid salt). To adjust its pH to 9.5-13, a suitable amount of a basic solution (e.g., NaOH or KOH) is added to the first solution. The order of salt concentration adjustment and pH adjustment is inconsequential. The mixture thus formed can then be kept under 4-40° C. for a sufficient period of time to allow salting-out of non-xanthohumol hop substances (e.g., chlorophyll, chlorophyll derivatives, and hop oily resins). After removing the salted-out substances, the pH value of the resultant solution is re-adjusted to 3-9 (e.g., 5-9 or 7-8), using, for example, an acidic solution such as HCl or $H_2SO_4$. The solution can be stirred slowly under 4-40° C. for a certain period of time (e.g., 30 minutes) to facilitate precipitation of xanthohumol. The precipitate thus formed is then collected and dried under vacuum. The resultant powder contains 40-95% by weight xanthohumol.

Optionally, the first solution mentioned above is first mixed with an aqueous salt solution to reach a salt concentration of 0.05 M to 0.3 M. Under this condition, hop substances such as chlorophyll are considerably salted out. After removing these substances, the resultant solution is subjected to the same steps as described above.

The xanthohumol-containing hop powder prepared by the method described above can be used for treating oxidative stress-associated medical conditions, such as cancer (e.g., breast, prostate, colon, and ovarian), aging, atherosclerosis, ischemic injury, inflammation, and neurodegenerative diseases (e.g., Parkinson's and Alzheimer's).

The hop powder described above also can be used for treating skin disorders, e.g., acne, rosacea, exzema, psoriasis, atopic dermatitis, contact dermatitis, seborrhea, sunburn, and skin aging. Without being bound by theory, xanthohumol, an active agent contained in the hop powder described herein, exerts its therapeutic effects in treating a skin disorder via the following two mechanisms: (1) xanthohumol quenches singlet oxygen, which causes or aggravates various skin disorders, e.g., acne, atopic dermatitis, and skin aging; and (2) xanthohumol inhibits growth of various gram positive bacteria, which is involved in development of acne and other skin diseases.

In addition, the xanthohumol-enriched hop powder is effective in treating inflammatory disease. An inflammatory disease is characterized by local or systemic, acute or chronic inflammation. Examples include retinopathy, inflammatory dermatoses (e.g., dermatitis, eczema, atopic dermatitis, allergic contact dermatitis, urticaria, necrotizing vasculitis, cutaneous vasculitis, hypersensitivity vasculitis, cosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD-associated with rheumatoid arthritis), asthma, and allergic rhinitis.

Moreover, the xanthohumol-enriched hop powder described herein is effective in treating diabetes (both type I and type II), obesity, viral infection, and bacterial infection, and is also effective in lowering plasma cholesterol levels in a subject.

To be used in any of the above-mentioned treatments, the hop powder can be mixed with a pharmaceutically acceptable carrier, and optionally with another therapeutically active agent, to form a pharmaceutical composition. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of the xanthohumol-containing pharmaceutical composition. Examples of other carriers include colloidal silicon oxide, magnesium stearate, cellulose, sodium lauryl sulfate, D&C Yellow # 10, microcrystalline cellulose, mannitol, glucose, defatted milk powder, polyvinylpyrrolidone, and starch, or a combination thereof. This pharmaceutical composition can then be presented in a variety of forms, such as tablet, capsule, powder, or liquid.

The xanthohumol-containing pharmaceutical composition can be administered to a subject in need of the treatment via suitable routes, e.g., oral administration, once or multiple times per day or administered once every several days. A solid formulation for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microglycolate, and alginic acid. Tablet binders that can be used include acacia, methylcellulose, sodium carboxymethylcellulose, polyvinylpyrrolidone (Povidone3), hydroxypropyl methylcellulose, sucrose, starch, and ethyl-cellulose. Lubricants that can be used include magnesium stearates, stearic acid, silicone fluid, talc, waxes, oils, and colloidal silica.

This solid formulation can be designed such that the composition is released in the intestine. For example, the composition is confined in a solid sub-unit or a capsule compartment that have respectively a matrix or a wall or a closure comprising an enteric polymer which dissolves or disperses at the pH of the small or large intestine to release the drag substance in the intestine.

In another example, the xanthohumol-containing hop powder is a component of a food product (e.g., yogurt, milk, or soy milk) or a food supplement (e.g., a nutrient supply or an herbal product). Such food products can be prepared by methods well known in the food industry.

When targeting a skin disorder, the xanthohumol-enriched hop powder described herein is preferred to be formulated in a manner suitable for topical administration, e.g., as a liquid and semi-liquid preparation that can be absorbed by the skin. Examples of a liquid and semi-liquid preparation include, but are not limited to, topical solutions, liniments, lotions, creams, ointments, pastes, gels, and emugels.

Topical solutions are homogeneous mixtures prepared by dissolving one or more active agents in a solvent. The solutions may contain other cosmeceutically acceptable chemicals to buffer, stabilize, or preserve the active agent(s). Solvents commonly used for preparation of topical solutions include ethanol, water, glycerol, and propylene glycol. Optionally, L-menthol can be added to a topical solution.

Lotions, preferably used for treating a large body area, are typically liquid or semiliquid preparations in which solid particles, including an active agent, are present in a water or alcohol base. They are usually suspensions of solids, and preferably, contain a liquid oily emulsion of the oil-in-water type. The insoluble matter in a lotion should be finely divided such that it applies to the skin surface without friction. Lotions typically contain suspending agents to produce better dispersions as well as compounds useful for localizing and holding the active agent(s) in contact with the skin, e.g., methylcellulose, sodium carbozymethyl-cellulose, or the like.

Creams are viscous liquid or semisolid emulsions, either oil-in-water or water-in-oil, containing cream bases. Cream bases are water-washable and contain an oil phase, an emulsifier, and an aqueous phase. The oil phase, also called the "internal phase," is generally comprised of petrolatum and a fatty alcohol such as cetyl or stearyl alcohol. The aqueous phase usually, although not necessary, exceeds the oil phase in volume, and contains a humectant. The emulsifier in a cream formulation can be a nonionic, anionic, cationic, or amphoteric surfactant. Exemplary surfactants include sorbitan esters or polyoxyethylene derivatives thereof (e.g., polyoxyethylene fatty acid esters) and carboxypolymethylene derivatives (e.g., carbopol).

Ointments are semisolid preparations that are typically based on petrolatum or other petroleum derivatives. Ointment bases should possess emolliency or other desirable features. As with other carriers or vehicles, they are preferably inert, stable, nonirritating, and nonsensitizing. There are four types of suitable ointment bases: oleaginous bases, emulsifiable bases, emulsion bases, and water-soluble bases. See Remington: The Science and Practice of Pharmacy, 19$^{th}$ Ed., at pages 1399 and 1404. Oleaginous ointment bases include, for example, vegetable oils, fats obtained from animals, and semisolid hydrocarbons obtained from petroleum. Emusifiable ointment bases, also known as absorbent ointment bases, contain little or no water and include, for example, hydroxystearin sulfate, anhydrous lanolin, and hydrophilic petrolatum. Emulsion ointment bases are either water-in-oil emulsions or oil-in-water emulsions, and include, but are not limited to, cetyl alcohol, glyceryl monostearate, lanolin, and stearic acid. Preferred water-soluble ointment bases are prepared from polyethylene glycols of varying molecular weights.

Pastes are semisolid dosage forms in which an active agent(s) is suspended in a suitable base. Depending on the nature of the base, pastes are divided between fatty pastes and those made from single-phase aqueous gels. The base in a fatty paste can be petrolatum, hydrophilic petrolatum, or the like. The pastes made from single-phase aqueous gels generally incorporate carboxymethylcellulose or the like as a base.

Gels and emugels both include a commonly known gel forming agent, such as cellulose derivatives (e.g., methyl cellulose, hydroxyethyl cellulose, and carboxymethyl cellulose), vinyl polymers (e.g., polyvinyl alcohols and polyvinyl pyrrolidones), carboxypoly-methylene derivatives (e.g., carbopol), pectins and gums (e.g., gum arabic and tragacanth, alginate, carrageenate, agar, or gelatin). The gel or emugel formulations may further contain an auxiliary agent commonly known in the art, such as a preservative, a stabilizer, a colorant, or a perfume.

The xanthohumol-containing topical formulations described above can further include one or more other active agents, such as a vitamin (e.g., vitamin B, 1,25-dihydroxy vitamin D3, vitamin K, vitamin A, and vitamin C), an antimicrobial agent (e.g., tolnaftate, ketoconazole, erythromycin, and tetracycline), an insect-repellent (e.g., aliphatic, cyclic or aromatic amides, citronella oil, terpineol, cineole, neem oil, and ethyl butyacetylaminopropionate), a self-tanning agent (e.g., dihydroacetone and lawsone), an anti-inflammatory agent (e.g., hydrocortisone, prednisone, prednisolone, aspirin, aloe vera, and mixtures thereof), a topical analgesic (e.g., lidocaine, benzocaine, butacaine, and clove oil), a skin redness reducer (e.g., guanidine derivatives and L-arginine derivatives).

Without further elaboration, it is believed that the above description has adequately enabled the present invention. The following examples are, therefore, to be construed as merely illustrative, and not limitative of the remainder of the disclosure in any way whatsoever. All publications cited herein are incorporated by reference.

EXAMPLE 1

Preparing a Xanthohumol-Rich Dry Hop Composition From Spent Hops Extracted Initially With Ethyl Acetate 1.45 kg spent hops from *Hallertau Hallertauer* were extracted with ethyl acetate, resulting in 82.6 g of a dark-green waxy crude hop extract after removal of the solvent. HPLC analysis showed that this crude hop extract contained 9.9 g xanthohumol, i.e., 12% by weight. The crude extract was dissolved in 1.5 L ethanol to generate an ethanol solution. 0.83 L NaCl (0.2 M) was then added to the ethanol solution to effect formation of a dark green oily precipitate, which was removed. The supernatant thus obtained was first mixed with a sufficient amount of NaOH such that its pH value reached 11.0. It was subsequently mixed with 2.5 L water and 1.0 L NaCl (2.75 M), resulting in the formation of a brown-colored precipitate. An orange-colored supernatant, obtained by filtering out the precipitate, was then produced. The pH value of this supernatant was adjusted to 8.0 with a sufficient amount of 25% $H_2SO_4$. A yellow precipitate thus formed was collected by filtration. The recovered precipitate was then dried under vacuum, resulting in yellow powder (11.3 g). HPLC analysis showed that the powder contained 66% by weight xanthohumol and 1.8% by weight iso-xanthohumol. No chlorophyll was detected in the yellow powder.

EXAMPLE 2

Preparing a Xanthohumol-Rich Dry Hop Composition from Spent Hops Extracted Initially with Acetone 200 g spent hops (containing 1.6 g xanthohumol, i.e., 0.8% by weight) from *Hallertau Hallertauer* were ground and extracted with 1.0 L acetone for 2 hours at 50° C. with overhead mixer agitation. The resultant extract was then filtered with a Buchner funnel and the residues were washed with 200 ml of acetone two times. The filtrates were collected and concentrated under vacuum at 50° C. to reach a total volume of about 60 ml. The concentrated extract was then mixed with 70 ml water and the solution thus formed was subjected to concentration under the same conditions to generate an acetone-free solution (70 ml). This solution was mixed with 130 ml ethanol and the resultant mixture was stirred at 50° C. for 30 minutes to ensure that all xanthohumol contained in the solution was completely dissolved. Subsequently, the solution was mixed with a suitable amount of 12 N NaOH gradually until its pH reached 11. Then, the solution was mixed with 320 ml water and 19.4 g KCl. After readjusting its pH to 11, the resultant mixture was subjected to filtration to remove the precipitate contained therein. The filtrate was collected, mixed with an appropriate amount of 25% $H_2SO_4$ to reach a pH value of 8.0, and then stirred very slowly for 30 minutes to effect formation of a yellow precipitate. This precipitate was collected by filtration, washed with about 30 ml water, and dried under vacuum at 50° C. for about 16 hours. The resultant powder, 2.522 g, contained 1.299 g xanthohumol (51.5% by weight). The overall yield of xanthohumol was 81%.

As shown below, the water solubility of the xanthohumol contained in the powder prepared by the method described above is much higher than the xanthohumol contained in hop compositions prepared by conventional methods.

The following three samples were suspended in water (1 mg xanthohumol/ml) to form three mixtures:
Sample 1: a xanthohumol-rich composition prepared by $CO_2$ extraction (containing
30% by weight xanthohumol);
Sample 2: a xanthonumol-rich composition prepared by silica gel chromatography
(containing 98% by weight xanthohumol), and
Sample 3: the powder described above in this Example, (containing 50% by weight xanthohumol)
After being sonicated for 5 minutes, the three mixtures were centrifuged at 3,000 rpm for 2 minutes or 12,000 rpm for 3 minutes. The supernatants thus formed were collected. 100 µl of each supernant were diluted with methanol, and then injected into HPLC to determine xanthohumol concentrations under the following conditions:

| HPLC system: | LC1100 series with Diode Array Detector (Agilent); |
|---|---|
| Mobile phase A: | 10 ml of 1M Triethylammonium acetate (TEAA) buffer (pH 7, #90357, Fluka) mixed with 990 ml of HPLC grade water (OmniSolv, EMD Chemicals); |
| Mobile phase B: | 10 ml of 1M TEAA buffer (pH 7, #90357, Fluka) mixed with 990 ml of HPLC grade acetonitrile (OmmniSolv, EMD Chemicals); |
| Column: | C18 end capped column 4.6 × 250 mm, 5 um (Capcell Pak C18 SG, Shiseido); |
| Column temperature: | 35° C. |
| Injection volume: | 20 uL |
| Flow rate: | 1 ml/min |
| Linear gradient: | from 30% B at 0 min to 90% B at 20 min and hold 90% B for 5 min |
| Read-out wavelength: | 370 nm |

The results thus obtained are shown in Table 1 below:

TABLE 1

Water Solubility of Xanthohumol Contained in Different Hop Compositions

| | Xanthohumol content (% by weight) | Solubility (µm, 3000 rpm) | Solubility (µm, 12000 rpm) |
|---|---|---|---|
| Sample 1 | 30 | 2.3 | 0.86 |
| Sample 2 | 98 | 6.0 | 2.3 |
| Sample 3 | 50 | 12.5 | 6.6 |

Clearly, the xanthohumol contained in Sample 3 (prepared by the method described above) has a significant high water solubility relative to the xanthohumol contained in hop compositions prepared by conventional $CO_2$ extraction or silica gel chromatography.

Further, the conversion of xanthohumol to isoxanthobumol in the following samples were tested:
Sample A: the hop powder prepared by the method described in this example.
Sample B: Sample 1 described above dissolved in cremophor EL (obtained from Sigma Chemical Co., St. Louis, Mo.) to form a solution with a xanthohumol concentration of 1% (w/v). See US Patent Application 2007/0248549.
Sample C: Sample 1 described above dissolved in cremophor EL to form a solution with a xanthohumol concentration of 4% (w/v). See US Patent Application 2007/0248549.
Samples A. B, and C were incubated at 75° C. for 120 hours and the content ratios between isoxanthohumol and xanthohumol in these samples were determined via HPLC before and after incubation and the ratios of isoxanthohumol/xanthohumol (IX/XN) were calculated.

The ratio of IX/XN is 0.03 in all of the three samples before the incubation. After the incubation, IX/XN of Sample A increased slightly to 0.04, indicating that only a small amount of xanthohumol was converted to isoxanthohumol during the incubation. Differently, the post-incubation IX/XN ratios of Samples B and C increased significantly to 0.2 and 0.3 respectively, indicating that a large amount of xanthohumol in each of the two samples was converted to isoxanthohumol during incubation. These results demonstrate that the xanthohumol contained in the hop composition prepared by the method of this invention is much more stable than that contained in hop compositions prepared by traditional methods.

EXAMPLE 3

Xanthohumol Inhibits Acne-Related Bacteria

Dried hop flowers (hops) have attracted a great deal of attention as a source of small molecules, such as humulones, lupulones, isohumulones and xanthohumol (FIG. 1) with potential for beneficial effects on health. The prior art has not shown that hops have in vitro biological activity against acne vulgaris. The present studies address the effects of hop components on biological factors involved in the pathogenesis of acne vulgaris.

The antibacterial effects of seven hops components against five different strains of bacteria involved in primary or secondary skin and soft tissue infections was evaluated, with broth dilution methods. Results of this analysis are shown at Table 1. The lowest MIC values against *P. acnes* and *S. pyogenes* were observed for lupulones 2, the values having reached 0.1 and 0.3 mg/ml, respectively (Table 1).

The lowest MIC values against *S. epidermidis, K. rhizophila*, and *S. aureus* were observed for lupulones 2 and xanthohumol 7, the value having reached 1 mg/ml. It is also important that all the strains are sensitive not only to naturally occurring hop components 1, 2, and 7, but also the chemically modified ones, 3, 4, and 5. Such strong inhibitory activities of lupulones 2 and xanthohumol 7 against acne-related bacteria have not been reported among natural products derived from edible plants. The low MIC values are comparable to the most commonly prescribed antibiotics for topical acne treatment (e.g., clindamycin and erythromycin). Interestingly, lupulones 2 and xanthohumol 7 exhibited bactericidal activity against *P. acnes* and the MBC values were 0.3 and 3.0 mg/ml, respectively (Table 2).

tively, whereas humulones 1 and lupulones 2 showed only weak activity with 27% and 28% inhibition for MMP-1, and 61% and 62% for MMP-8, respectively. Chemically modified derivatives 3, 4, 5, and 6 did not show activity up to a concentration of 100 mg/ml.

Extracellular proteases, in particular MMPs, have been implicated in a number of dermatological conditions; for example, in chronological aging, inflammatory matrix remodeling, and hyperproliferative skin disorders (Choi et al. 2008 J. Invest. Dermatol. 128: 846-854). These processes involve the increased breakdown of various components of the extracellular matrix in the skin, notably collagen, elasti, and fibronectin. Enhanced expression of the collagenases MMP-1 and -8 has been described as playing a central role in connective type-1 collagen breakdown in the skin (Brenneisen et al. 2002 Ann. NY Acad. Sci. 973: 31-43). The transcription factors nuclear factor 1-B (NFkappaB) and activator protein-1 (AP-1) are activated in acne lesions with consequent elevated expression of their target gene products, inflammatory cytokines and matrix-degrading metalloproteinases, respectively. These elevated gene products are molecular mediators of inflammation and collagen degradation in acne lesions in vivo. Recently, this new knowledge has enabled a rational strategy for the development of drugs that can target the inflammation and matrix remodeling that occurs in severe acne (Kang et al. 2005 μm. J. Pathol. 166: 1691-1699).

TABLE 2

Antibacterial activities (MIC[a] and MBC[b]) of hop components against the most common bacteria causing primary or secondary skin or soft tissue infections

| Compound | MIC (μg/mL) [MBC (μg/mL)] | | | | |
|---|---|---|---|---|---|
| | P. acnes | S. aureus | S. epidermidis | S. pyogenes | K. rhizophila |
| Humulones (1) | 10 [30] | 10 [100] | 10 [100] | 3 [100] | 30 [100] |
| Lupulones (2) | 0.1 [0.3] | 1 [100] | 10 [10] | 0.3 [30] | 1 [10] |
| Isohumulones (3) | 30 [>100] | 10 [>100] | 30 [>100] | 10 [>100] | 100 [100] |
| Reduced isohumulones (5) | 30 [>100] | 30 [>100] | 10 [>100] | 10 [>100] | ND [ND] |
| Tetrahydro-isohumulones (4) | 3 [10] | 3 [>100] | 10 [>100] | 10 [>100] | ND [ND] |
| Hexahydro isohumulones (6) | 3 [100] | 10 [>100] | 10 [100] | 3 [>100] | ND [ND] |
| Xanthohumol (7) | 3 [3] | 1 [100] | 3 [10] | 1 [3] | 1 [10] |

ND: Not Determined
[a]MIC indicates minimal 100% inhibitory concentration.
[b]MBC indicates the lowest concentration required to kill an organism

EXAMPLE 4

Xanthohumol has Anti-Collagenase Activity

Results of activity against interstitial collagenase (MMP-1) and neutrophil collagenase (MMP-8) are listed in Table 3.

TABLE 3

Anticollagenase activities[a] of hops against MMP-1 and MMP-8 involved in acne pathogenesis

| Compound | Concentration (μg/mL) | Inhibitory ratio (%) | |
|---|---|---|---|
| | | MMP-1 | MMP-8 |
| Humulones (1) | 100 | 62 | 62 |
| | 30 | 11 | 29 |
| Lupulones (2) | 100 | 27 | 28 |
| | 30 | 6 | 12 |
| Isohumulones (3) | 100 | 0 | 0 |
| Reduced isohumulones (5) | 100 | 0 | 0 |
| Tetrahydroisohumulones (4) | 100 | 0 | 0 |
| Hexahydroisohumulones (6) | 100 | 0 | 0 |
| Xanthohumol (7) | 100 | 91 | 99 |
| | 30 | 65 | 70 |
| | 10 | 25 | 31 |

[a]Data represent the mean of three independent measurements

Xanthohumol 7 showed the highest activity against both collagenases; the $IC_{50}$ values were 20.5 and 16.8 mg/ml, respec-

EXAMPLE 5

Xanthohumol has Antioxidant Activity

It is well documented that inflammation caused by oxidative damage has been implicated in not only in skin disorders, but also in various systemic chronic diseases, such as cancer, Alzheimer's disease, rheumatoid arthritis, cardiovascular disease, cataracts, and other ageing processes. Reactive oxygen species are essential intermediates in oxidative metabolism. Nonetheless, when generated in excess, ROS in various active forms can damage tissues. The radical-scavenging activity of hop components 1 and 2 has been evaluated previously using a conventional 1,1-Diphenyl-2-picrylhydrazyl (DPPH) assay, employing one of the stable nitrogen-centered free radicals. These components have promise for their antioxidant potential. Xanthohumol was also shown to scavenge hydroxyl and peroxyl radicals, and superoxide anion radicals, in an oxygen radical absorbance capacity (ORAC) assay (Gerhauser 2005 Mol. Nutr. Food Res. 49: 827-831; Vogel et al. 2008 Bioorg. Med. Chem. 16: 4286-4293).

A standardized ORAC value shows the scavenging capacity of antioxidants against the peroxyl radicals, which are among the most common ROS found in the body. Thus the ORAC method has become a widely used method for assessing antioxidant capacity in biological samples and foods. However, because of its inability to measure both hydrophilic and lipophilic antioxidants, the method has its limitations.

An ORAC method for lipophilic antioxidants was further developed and validated using fluorescein as the fluorescent probe (Prior et al. 2003 J. Agric. Food Chem. 51: 3273-3279). This method has the advantage that similar assay conditions and standards can be used for both hydrophilic and lipophilic antioxidant components, such that the two values can be added together to obtain a total antioxidant capacity.

Table 4 shows six assays for the antioxidant capacity of hop components against various ROS formed in human skin (Bickers and Athar 2006 J. Invest. Dermatol. 126: 2565-2575).

TABLE 4

Reactive oxygen species (ROS) related to inflammation

| | ROS | Assay |
|---|---|---|
| 1 | Peroxyl nitrite | NORAC |
| 2 | Hydroxyl radical | HORAC |
| 3 | Peroxyl radical, fat-soluble | ORAC-L |
| 4 | Peroxyl radical, water-soluble | ORAC-H |
| 5 | Superoxide | SOD |
| 6 | Heavy metal cation $Fe^{3+}$ | FRAP |
| 7 | Singlet oxygen $^1O_2$. | SOAC |

ORAC-H: $ORAC_{hydro}$, water-soluble antioxidant capacity
ORAC-L: $ORAC_{lipo}$, lipid soluble antioxidant capacity In the present work, the ORAC value is expressed as the sum of values of both the water-soluble and fat-soluble parts. Green tea catechins (Polyphenon 60) were used as the control with the highest ORAC value among edible plants. Vitamin C and vitamin E were used as controls for water- and fat-soluble molecules, respectively.

The results of these studies are shown in Table 5.

TABLE 5

Oxygen radical absorbance capacity (ORAC) of hop components

| Conpound | ORAC-H (Trolox equivalent) | ORAC-L (Trolox equivalent) | ORAC-Total (Trolox equivalent) |
|---|---|---|---|
| Humulones (1) | 0.62 | 0.60 | 1.2 |
| Lupulones (2) | 0.84 | 1.1 | 1.9 |
| Isohumulones (3) | 0.41 | 0.054 | 0.46 |
| Reduced isohumolones (5) | 0.64 | 0.062 | 0.65 |
| Tetrahydro-isohumulones (4) | 0.034 | 0.011 | 0.045 |
| Xanthohumol (7) | 2.1 | 2.1 | 4.2 |
| Vitamin C | 1.4 | — | 1.4 |
| Vitamin E | — | 0.75 | 0.75 |
| Polyphenon 60 | 4.2 | 0.006 | 4.2 |

ORAC-Total: $ORAC_{lipo}$ + $ORAC_{hydro}$
— No activity detected

The higher the total ORAC score, the higher the antioxidant capacity. The total ORAC value of xanthohumol 7 was comparable to that of Polyphenon 60, and much higher than that of vitamins C and E. In addition xanthohumol 7 shows equal activity in both fat- and water-soluble antioxidant capacity. These data indicate that xanthohumol 7 may serve as a well-balanced antioxidant similar to the combination of vitamins C and E. Taken altogether, the antioxidant properties of xanthohumol 7 deserve attention.

EXAMPLE 6

Xanthohumol has Singlet Oxygen-Quenching Activity

Table 6 shows the singlet oxygen-quenching activity of hop components.

TABLE 6

Singlet oxygen absorbance capacity (SOAC) of hop components

| Compound | SOAC (Vitamin E equivalent) |
|---|---|
| Humulones (1) | 0.75 |
| Lupulones (2) | 0.80 |
| Isohumulones (3) | 0.40 |
| Reduced isohumolones (5) | 0.55 |
| Tetrahydro-isohumulones (4) | 0.59 |
| Xanthohumol (7) | 14.1 |
| Vitamin E | 1.0 |
| Polyphenon 60 | 1.8 |

Alpha-tocopherol (vitamin E) was used as the calibration standard, and the SOAC result is expressed as mmol VtE/g. The higher the SOAC score, the higher the singlet oxygen-quenching capacity. Interestingly, the xanthohumol SOAC value was about 8-15 times higher than that of vitamin E or Polyphenon 60. Singlet oxygen has been postulated to be a highly reactive and toxic intermediate against skin. It is known that the acne-causing bacterium *P. acnes* naturally produces high amounts of intracellular porphyrins, mostly coproporphyrin. Singlet oxygen can be generated on the skin surface from *P. acnes* porphyrins under sunlight and induce serious skin damage (Arakane et al. 1996 Biochem. Biophys. Res. Commun. 223: 578-582). Various skin disorders progress through a singlet oxygen-dependent mechanism, including acne, atopic dermatitis, and skin aging.

Squalene is also a component of acne sebum. Both porphyrins and squalene are directly exposed to the external environment and play a key role in skin physiology. Recently it was demonstrated that squalene peroxidation during solar exposure is mainly caused by singlet oxygen and by free radical attack, suggesting that sun skin-care cosmetics should make use not only of free radical scavengers but also of singlet oxygen quenchers (Auffray 2007 Int. J. Cosmet. Sci. 29: 23-29). Xanthohumol's singlet oxygen-quenching activity might be widely used to develop new therapeutic medications for immune and inflammatory diseases (Moan and Juzenas 2006 J. Environ. Pathol. Toxico. Oncol. 25: 29-50).

Recently many scientific papers have addressed the relationship between lifestyle diseases and chemical attacks by singlet oxygen and free radicals. As evidenced by the results reported herein, xanthohumol is among the most powerful naturally occurring antioxidants in terms of singlet oxygen-quenching activity. The results provided herein indicate that xanthohumol's singlet oxygen-quenching activity comes close to that of β-carotene, a precursor of retinoids.

Figure 2:
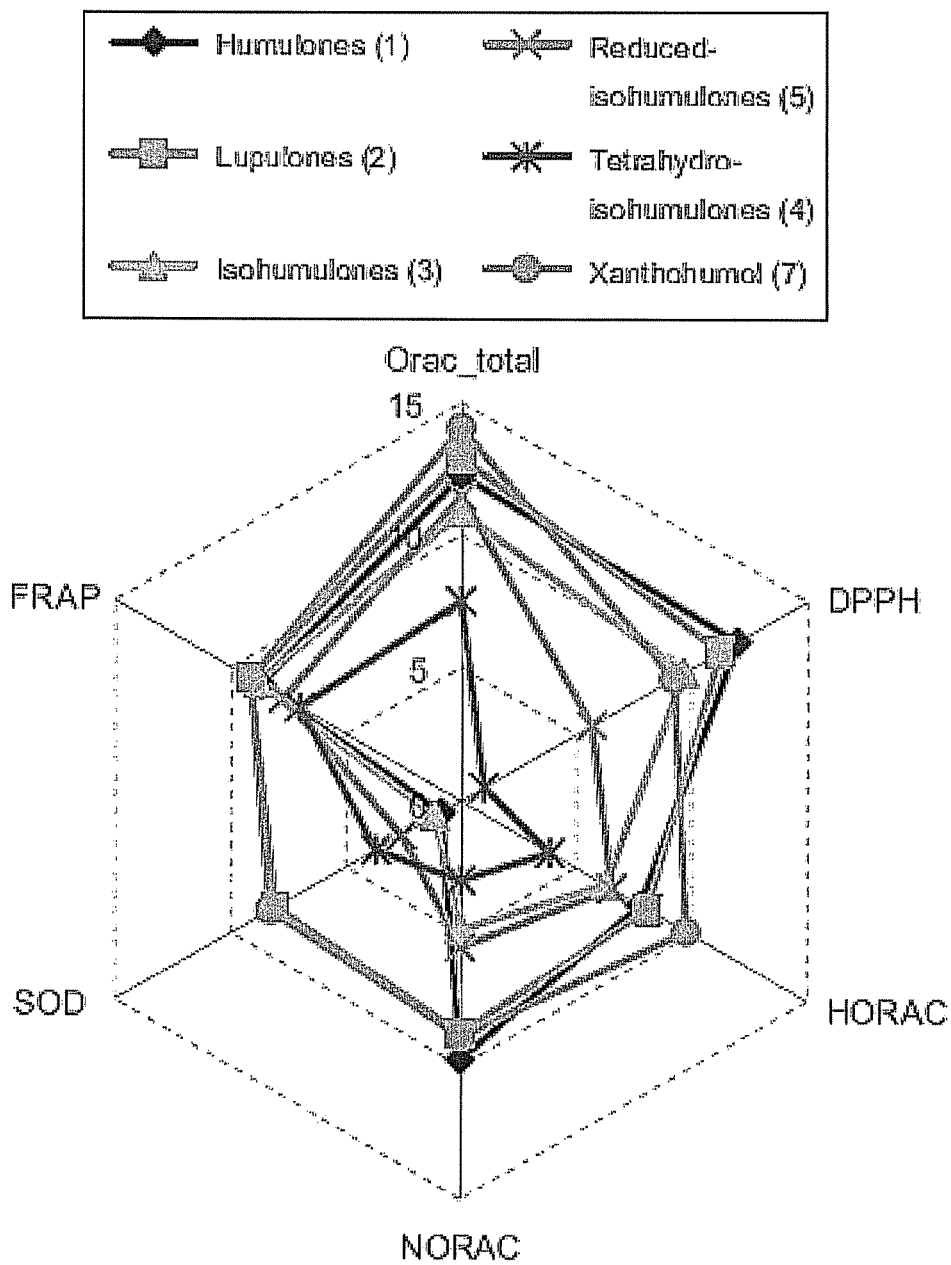
FIG. 2 provides a graphical representation of antioxidant activities of hop components in six assay categories.

The radar chart in FIG. 2 shows how the hop components ranked in the six antioxidant assays described herein. The SOAC scores are not included in this figure; ORAC values used are the sum of lipophilic and hydrophilic results. For each assay category, scaling was made logarithmic so that the plot on the chart resembles the associated rating. The chart graphically shows areas of relative strength and relative weakness, as well as depicting the general overall antioxidative capacity. The larger the spatial area, the higher the overall antioxidative capacity. Significantly, xanthohumol 7 (green) shows the highest quenching activity against peroxyl radical (ORAC-total), superoxide (SOD), ferric ion (FRAP), and hydroxyl radical (HORAC). Humulones 1 (yellow) show the strongest quenching activity against the nitrite radical (NO-RAC) and DPPH.

On the other hand, chemically reduced derivatives 3, 4, and 5 show poor antioxidant capacity in comparison to natural compounds. As active ingredients with anti-inflammatory activity due to their improved chemical stability and ease of handling, chemically reduced hop derivatives 4, 5, and 6 are used for relief of arthritis symptoms. The chemical modifications significantly impair one of the most important biological properties essential for anti-inflammatory efficacy, antioxidant capacity (Altindag et al. 2007 Rheumatol Int. 27:339-344).

In this study, biological assays were used to explore how hops extracts alter three activities involved in acne pathogenesis: bacterial proliferation, increased sebum production caused by reactive oxygen species, particularly singlet oxygen, and excessive matrix remodeling through type-1 collagen breakdown by MMPs.

Over-the-counter and other nonprescription medications are often more effective when they modulate two or more of these activities when treating acne. As a result, dermatologists have generally concluded that taking a more comprehensive approach gives better results. Thus the recommendations given to patients frequently suggest using more than one agent at a time. Unfortunately, mixing medications does not always work because of unwanted interactions that lead to a decrease in or loss of efficacy.

Results reported here confirm that xanthohumol 7 and lupulones 2 demonstrate multiple activities against the main biological events responsible for the pathogenesis of acne. It is clear that the anti-inflammatory activity of naturally occurring hop components inhibits the proinflammatory mediators (e.g., COX-2, PGE2, NO, NFkappaB, IL-1β, and TNF-α) responsible for skin inflammation. Thus, the unique multifunctional activities of lupulones 2 and xanthohumol 7 among hop components, could prove to be of value for future human clinical studies in comparison with commercial combinations of synthetic drugs.

Hop Components

With reference to FIG. 1, three compounds, humulones 1, lupulones 2 and xanthohumol 7 are naturally occurring hop components. Isohumulones 3 are isomerized molecules that are converted from humulones 1. Other molecules, tetrahydroisohumulone 4, reduced isohumulone 5, and hexahydroisohumulone 6, are hydrogenated derivatives of isohumulones 3 with improved stability. The humulones-rich fraction (containing 34% of humulones 1; calcd for $C_{21}H_{30}O_6$) was produced by fractionation of a $CO_2$ extract (obtained from John I Haas Inc., Yakima, Wash.) followed by purification through a column packed with Amberlite 20 FPX66 (food grade), with alkaline water used as an eluent aqueous at pH 10. The lupulones-rich fraction (containing 10% of lupulones 2; calcd for $C_{26}H_{38}O_4$) was produced by fractionation of the $CO_2$ extract, followed by purification through active charcoal treatment in an aqueous solution at pH 10.

Isohumulones 3 (calcd for $C_{21}H_{30}O_5$, 10% aqueous solution) converted by treatment of humulones 1 at 70° C. under alkaline conditions, were also obtained from John I Haas Inc. Reduced isohumolones 5 (calcd for $C_{21}H_{32}O_5$), synthesized by reduction of isohumulones 3 with sodium borohydride ($NaBH_4$) in water at pH 10, were likewise obtained from John I Haas Inc. Similarly obtained were tetrahydro- and hexahydroisohumulones 4 (calcd for $C_{21}H_{32}O_5$) and -6 (calcd for $C_{21}H_{34}O_5$), prepared by hydrogenation of isohumulones 3, and reduced isohumulones 5 respectively, in the presence of 5% palladium on charcoal (Pd/C) in water at pH 10.

A xanthohumol-rich fraction (containing 50% of xanthohumol 7, calcd for $C_{21}H_{22}O_5$) was prepared by extraction of spent hops (obtained from Nateco2, Wolnzach, Germany) with acetone, and subsequent purification by a pH-adjusted salting-out method employing aqueous ethanol in the presence of NaCl.

Antimicrobial Assays

Antimicrobial susceptibility testing was performed using a broth dilution method. Gentamicin or ampicillin was used as a control to verify the methodology. A stock solution (20 mg/ml) of the test substance (or vehicle control) was prepared in dimethyl sulfoxide. Serial dilution was done in microwell plates. Reinforced Clostridial Medium was used for *P. acnes* (ATCC 6919). Three hundreds ml of the test substance was added to the test tube containing *P. acnes* ($10^5$ CFU/ml) in 2.7 ml of cultures grown under anaerobic conditions. Mueller-Hinston Broth suitable for culturing *S. epidermidis* (ATCC 12228), *K. rhizophila* (formerly *M. luteus*) (ATCC 9341), and *S. aureus* (ATCC 6538P), and Brain Heart Infusion Broth suitable for culturing *S. pyogenes* (ATCC 14289) were used. A total of 100 ml of the test substance was added to the test tube containing the other microorganisms ($10^5$ CFU/ml) in 0.9 ml of cultures grown under controlled conditions. After 2 days for acnes and 1 day for the others, growth of the culture was examined and scored positive for inhibition of growth, or negative for no effect upon growth. Samples from those tubes that scored positive was plated onto an agar plate and incubated under controlled conditions. The minimum inhibitory concentration (MIC) was defined as the lowest concentration that resulted in no visible growth after 2 days for *P. acnes* or 1 day for the others. The minimum bactericidal concentration (MBC) was defined as the lowest concentration at which the microorganisms failed to grow in each medium and on each agar plate.

Antioxidant Assays

Both hydrophilic and lipophilic oxygen radical absorbance capacity (ORAC) assays were carried out at Brunswick Laboratory (Wareham, Mass.) based on the modified ORACfl method reported by Ou et al. (2001 J. Agric. Food Chem. 49: 4619-4626, 2002 J. Agr. Food Chem. 50: 3122-3128). Trolox, a water-soluble vitamin E analog, was used as the calibration standard. The data are expressed as mmole of Trolox equivalents per gram (mmol TE/g). The acceptable precision of the ORAC assay is a 15% relative standard deviation. Caffeic acid was used as the calibration standard. Hydroxyl radical ORAC (HOR-AC) is expressed as mmole caffeic acid equivalent per gram (mmol CAE/g). Trolox was used as the calibration standard. The peroxyl nitrite ORAC (NORAC) result is expressed as mmol TE/g. Alpha-tocopherol (vitamin E) was used as the calibration standard, and the singlet oxygen absorbance capacity (SOAC) result is expressed as mmole a-tocopherol equivalent (mmol VtE) per gram (Aubry et al. 1989 J. Org. Chem. 54: 726-728). The abbreviation for the 1,1-diphenyl-2-picrylhydrazyl radical is DPPH. Radical-scavenging activity was measured by the change in absorbance at 517 nm with the DPPH result expressed as mmol TE/g. Similarly, FRAP is an abbreviation for the ferric reducing antioxidative power method, which utilizes chemical conversion of the yellow Fe 3+−2,4,6-tripyridyl s-triazine (TPTZ) complex to the blue Fe 2+-TPTZ complex by electron donation under acidic conditions (Okada and Okada 1998 J. Agric. Food Chem. 46: 401-406). The FRAP result is expressed as mmol TE/g (Ou et al. J. Agric. Food Chem. 49: 4619-4626). Superoxide dismutase (SOD) was used as a calibration standard; the SOD result is expressed as kilo unit SOD equivalent (kunitSODeq) per gram.

Anticollagenase Assays

Human recombinant matrix metalloproteinase-MMP-1) pro-enzyme, expressed in mammalian cells, and human nutrophil MMP-8 pro-enzyme were activated with 4-aminophenylmercuric acetate for 60 min 37° C., respectively (Knight et al. 1992 FEBS Lett. 296: 263-266). Hop components and vehicle were preincubated with 5 mM MMP- and 6 nM MMP-8 active enzymes in a modified MOPS buffer, pH 7.2, for 60 minutes at 37 C. The reaction was initiated by addition of 4 mM Mca-Pro-Leu-Gly-Leu-Dpa-Ala-Arg for another 120-minute incubation period. The determination of the amount of Mca-Pro-Leu-Gly formed was read spectrofluorimetrically at 340/400 nm. Tissue inhibitors of metalloproteinase TIMP-1 and TIMP-2 were used as positive controls (Olson et 1997 J. Biol. Chem. 272: 29975-29983).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An aqueous xanthohumol and isoxanthohumol composition extracted from hops formulated for topical administration which is prepared by a process comprising: providing a first solution containing hops and a first solvent, wherein the hops include 0.4-20% by weight xanthohumol and the first solvent includes up to 90% by volume water and at least 3% by volume a water miscible solvent;

adjusting the salt concentration of the first solution from 0.05 M to 5.0 M and the pH value of the first solution from 10.5 to 12.0 to produce a first precipitate;

removing the first precipitate to obtain a second solution; adjusting the pH of the second solution from 7 to 8 to produce a second precipitate;

and collecting the second precipitate, wherein the second precipitate contains the aqueous xanthohumol and isoxanthohumol composition extracted from hops wherein the composition contains 40-95% by weight xanthohumol and wherein the composition comprises an isoxanthohumol/xanthohumol ratio that is 0.01-0.5.

2. The composition of claim 1, wherein the isoxanthohumol/xanthohumol ratio is 0.03 or 0.04.

3. The composition of claim 1, wherein the composition comprises at least about 50% or 75% by weight xanthohumol and about 0.4-4.5% by weight isoxanthohumol.

4. The composition of claim 1, wherein the composition is a topical formulation selected from the group consisting of a solution, liniment, lotion, cream, ointment, paste, gel, and emugel.

5. The composition of claim 1, wherein the composition further comprises a vitamin selected from the group consisting of vitamin B, 1,25-dihydroxy vitamin D3, vitamin K, vitamin A, and vitamin C.

6. The composition of claim 1, wherein the composition further comprises an anti-microbial agent selected from the group consisting of tolnaftate, ketoconazole, erythromycin, and tetracycline.

7. The composition of claim 1, wherein the composition further comprises an insect-repellent selected from the group consisting of aliphatic, cyclic amides, aromatic amides, citronella oil, terpineol, cineole, neem oil, and ethyl butyacetylaminopropionate.

8. The composition of claim 1, wherein the composition further comprises a self-tanning agent selected from the group consisting of dihydroacetone and lawsone.

9. The composition of claim 1, wherein the composition further comprises an anti-inflammatory agent selected from the group consisting of hydrocortisone, prednisone, prednisolone, aspirin, aloe vera, and mixtures thereof.

10. The composition of claim 1, wherein the composition further comprises a topical analgesic selected from the group consisting of lidocaine, benzocaine, butacaine, and clove oil.

* * * * *